(12) United States Patent
Kimura et al.

(10) Patent No.: US 8,337,396 B2
(45) Date of Patent: Dec. 25, 2012

(54) ENCAPSULATED MEDICAL DEVICE GUIDANCE SYSTEM, AND A METHOD OF CONTROLLING THE SAME

(75) Inventors: Atsushi Kimura, Akiruno (JP); Akio Uchiyama, Yokohama (JP); Masatoshi Homan, Hino (JP)

(73) Assignee: Olympus Medical Systems Corp., Tokyo (JP)

( * ) Notice: Subject to any disclaimer, the term of this patent is extended or adjusted under 35 U.S.C. 154(b) by 1187 days.

(21) Appl. No.: 12/146,725

(22) Filed: Jun. 26, 2008

(65) Prior Publication Data

US 2008/0300459 A1 Dec. 4, 2008

Related U.S. Application Data

(63) Continuation of application No. PCT/JP2006/326147, filed on Dec. 27, 2006.

(30) Foreign Application Priority Data

Dec. 27, 2005 (JP) ................. 2005-375538

(51) Int. Cl.
  *A61B 1/00* (2006.01)
  *A61B 1/04* (2006.01)
(52) U.S. Cl. ...................... 600/117; 600/118
(58) Field of Classification Search ............. 600/109, 600/117–118, 160, 302
See application file for complete search history.

(56) References Cited

U.S. PATENT DOCUMENTS

| | | | | |
|---|---|---|---|---|
| 5,681,260 A | * | 10/1997 | Ueda et al. | 600/114 |
| 6,480,099 B1 | * | 11/2002 | Ziegler | 340/10.1 |
| 7,182,089 B2 | * | 2/2007 | Ries | 128/899 |
| 2004/0236180 A1 | | 11/2004 | Uchiyama et al. | |
| 2005/0004473 A1 | * | 1/2005 | Fujita et al. | 600/476 |
| 2005/0062562 A1 | | 3/2005 | Ries | |
| 2007/0244388 A1 | * | 10/2007 | Sato et al. | 600/424 |
| 2008/0188712 A1 | * | 8/2008 | Shimizu et al. | 600/118 |
| 2008/0306358 A1 | * | 12/2008 | Minai | 600/302 |

FOREIGN PATENT DOCUMENTS

| | | |
|---|---|---|
| JP | 2003-135389 | 5/2003 |
| JP | 2004-255174 | 9/2004 |
| JP | 2005-130943 | 5/2005 |

* cited by examiner

*Primary Examiner* — Philip R Smith
(74) *Attorney, Agent, or Firm* — Scully Scott Murphy & Presser, PC

(57) ABSTRACT

An encapsulated medical device system according to an embodiment of the present invention includes a selector between a receiving device and a plurality of receiving antennas having their respective directionalities. The system selects and disconnects any receiving antenna subjected to the effect of a magnetic field used to guide a capsule endoscope, and captures information about the inside of a body from the appropriate receiving antenna thus selected. The system prevents an overload current caused by induced voltage from being applied to the receiving device. The system includes the function of preventing the overload current, caused by induced voltage arising from a sudden movement of the capsule endoscope or sudden change in magnetic field gradient, from being applied to a transmission circuit of the capsule endoscope and a receiving device.

11 Claims, 5 Drawing Sheets

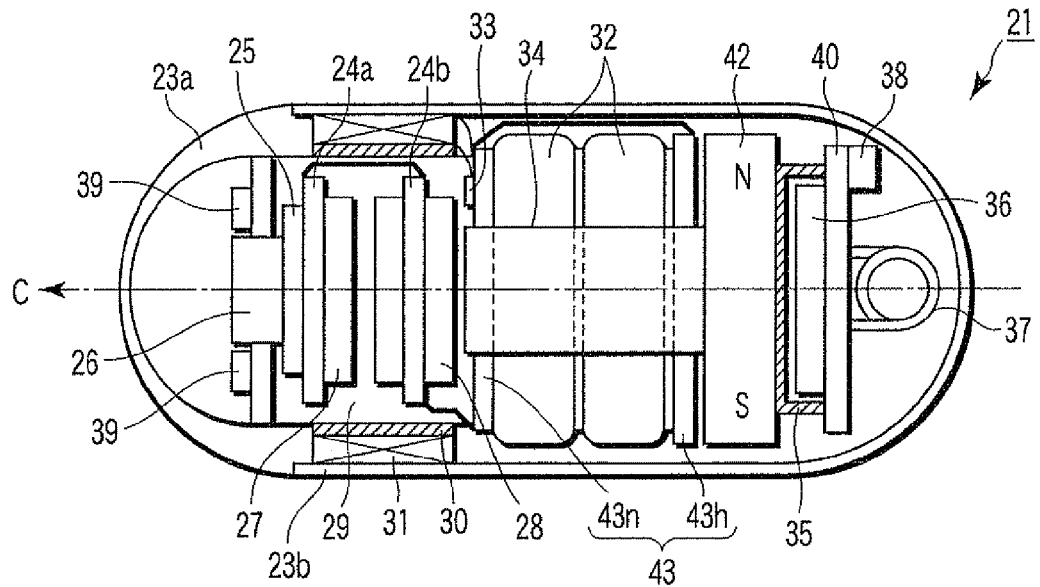
F I G. 2
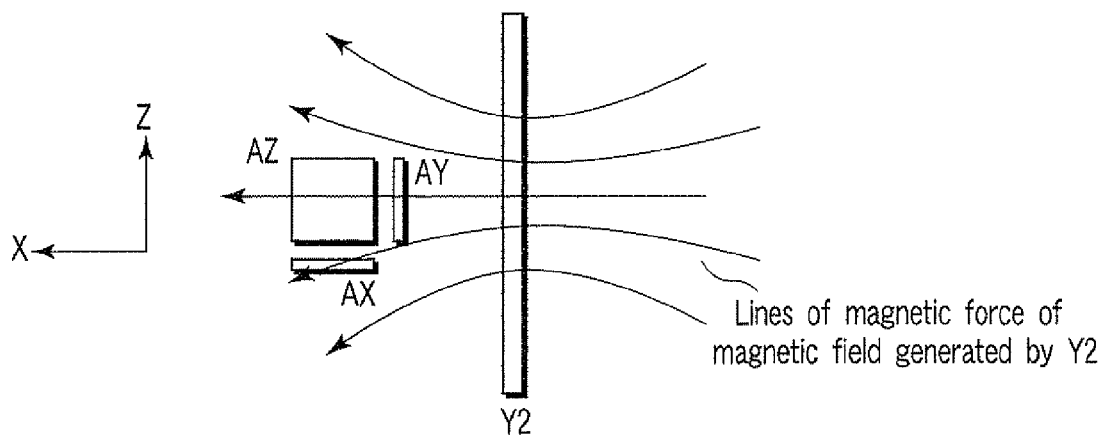
F I G. 3

ENCAPSULATED MEDICAL DEVICE GUIDANCE SYSTEM, AND A METHOD OF CONTROLLING THE SAME

CROSS REFERENCE TO RELATED APPLICATIONS

This is a Continuation Application of PCT Application No. PCT/JP2006/326147, filed Dec. 27, 2006, which was published under PCT Article 21(2) in Japanese.

This application is based upon and claims the benefit of priority from prior Japanese Patent Application No. 2005-375538, filed Dec. 27, 2005, the entire contents of which are incorporated herein by reference.

BACKGROUND OF THE INVENTION

1. Field of the Invention

The present invention relates to a guidance system for an encapsulated medical device inserted into an intracavital for obtaining internal biological information, and a method of controlling the same.

2. Description of the Related Art

An encapsulated medical device is known as a medical device that captures internal biological information. The medical device periodically transmits the internal biological information includes image data captured by imaging, for example, the medial wall while the medical device moving in an intracavital.

An example of such the encapsulated medical device is disclosed in Jpn. Pat. Appln. KOKAI Publication No. 2004-255174, which proposes a medical device guidance system capable of magnetically inducing a capsule endoscope. This medical device guidance system is designed as described below. A capsule endoscope body with a spiral projection formed on its periphery incorporates a magnet polarized perpendicularly to the length of the capsule endoscope body (i.e., the axis of the cylinder). The capsule body is rotated by a magnetic field generated by a magnetic field control device and a rotating magnetic field generation device based on operating instructions. Simultaneously with the rotation, the capsule body is moved such that its moving direction changes smoothly, and it images required parts. The image data captured by imaging the required parts are transmitted by radio to a radio circuit (antenna) on the medical device main body side from a radio circuit (antenna) disposed in the capsule endoscope.

BRIEF SUMMARY OF THE INVENTION

An embodiment according to the present invention provides an encapsulated medical device guidance system which includes a plurality of receiving antennas of different directionalities and selects a receiving antenna appropriate to receive information about the inside of a body transmitted from an encapsulated medical device, and a control method for the system.

An encapsulated medical device guidance system according to a first aspect of the invention comprises: an encapsulated medical device having an internal biological information acquisition unit to acquire internal biological information, a communication unit to output the acquired internal biological information to the outside as an output signal, and a magnet; a plurality of receiving antennas which are different from one another in a direction in which receiver sensitivity in a directionality thereof is highest and receive the output signal; a selector which is connected to said plurality of antennas and selects a path for the signal; a receiving device which is connected to the selector and receives the signal from the selected receiving antenna; a magnetic field generating unit which causes the magnet to act, thereby generating an induction magnetic field for moving the encapsulated medical device in a target direction; and a control unit which controls a signal generated by the magnetic field generating unit, wherein the control unit specifies a receiving antenna in which an overload current flows on account of the induction magnetic field, and disconnects the receiving antenna from the receiving device.

An encapsulated medical device guidance system according to a second aspect of the invention comprises: an encapsulated medical device having an internal biological information acquisition unit to acquire internal biological information, a communication unit to output the acquired internal biological information to the outside as an output signal, and a magnet; a plurality of receiving antennas which receive the output signal; a magnetic field generating unit which causes the magnet to act, thereby generating an induction magnetic field for moving the encapsulated medical device in a target direction; and a control unit which controls a signal generated by the magnetic field generating unit, the encapsulated medical device guidance system further comprising an antenna control element which, based on an intensity of the induction magnetic field in proximity of at least one of the receiving antenna and the transmission antenna, changes electrical characteristics of the antenna.

A third aspect of the invention provides a method for controlling a system for inducing an method for controlling a system for inducing an encapsulated medical device which transmits information about the inside of a body cavity while moved in a target direction within the body cavity by a magnetic field generated by a magnet disposed in the encapsulated medical device, wherein one of a plurality of receiving antennas oriented in different directions is selected according to receiver sensitivity to the transmitted information about the inside of the body, thereby receiving the information about the inside of the body, and the receiving antenna in which an overload current flows on account of the magnetic field is disconnected from a receiving path.

BRIEF DESCRIPTION OF THE SEVERAL VIEWS OF THE DRAWING

The accompanying drawings, which are incorporated in and constitute a part of the specification, illustrate embodiments of the invention, and together with the general description given above and the detailed description of the embodiments given below, serve to explain the principles of the invention.

FIG. 2 a sectional view showing the configuration of a first capsule endoscope according to the embodiment;

FIG. 3 shows an interrelation between a receiving antenna according to the embodiment and lines of magnetic force generated by a guidance coil;

DETAILED DESCRIPTION OF THE INVENTION

An embodiment according to the present invention will hereinafter be described with reference to the accompanying drawings.

Figure 1:
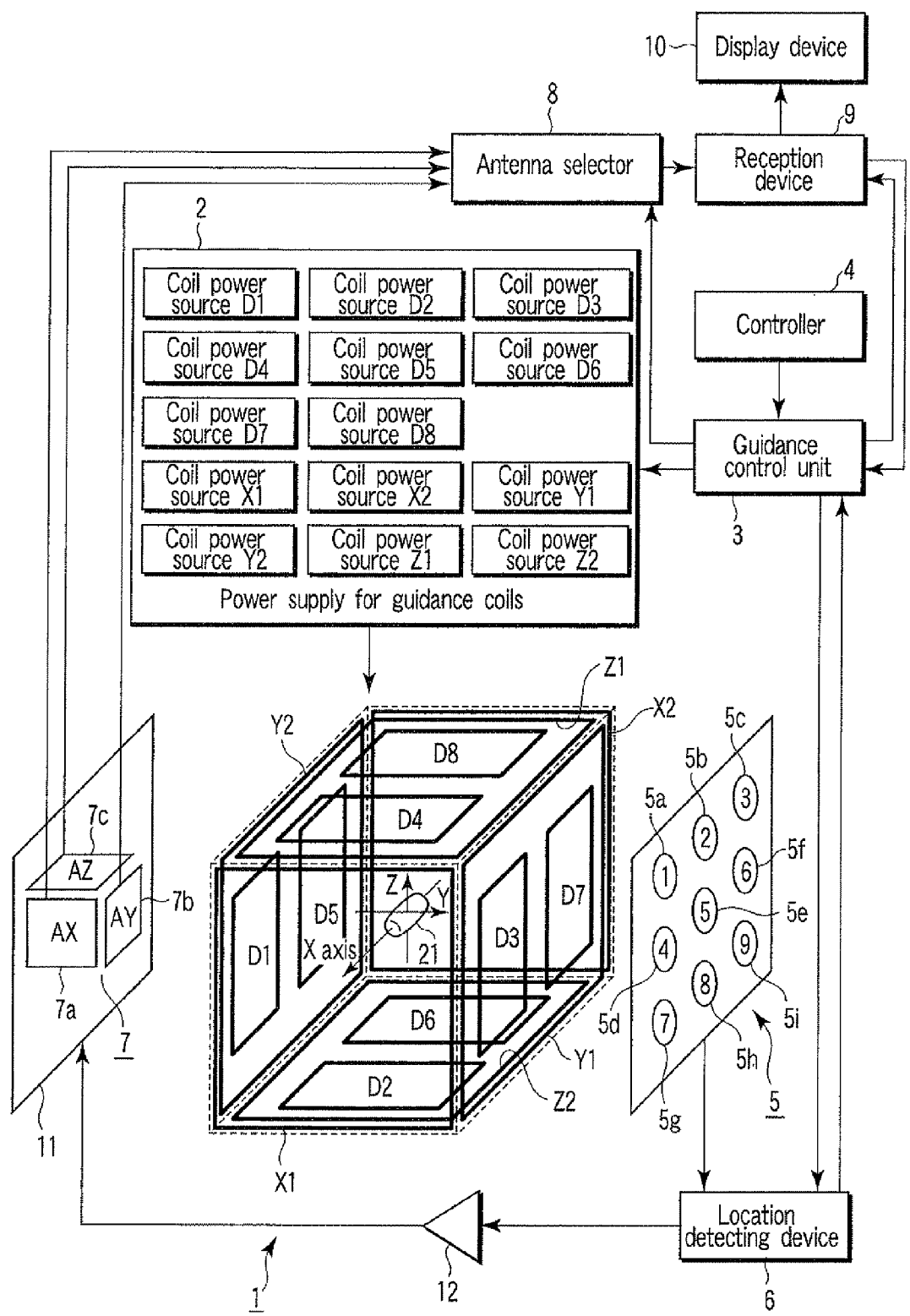
FIG. 1 shows the configuration of an encapsulated medical device guidance system according to an embodiment of the present invention.

First, there will be described an encapsulated medical device guidance system according to an embodiment of the present invention, which is shown in FIG. 1. FIG. 2 is a sectional view of the configuration of a capsule endoscope according to the present embodiment.

The encapsulated medical device guidance system is roughly divided into a capsule endoscope 21 and a magnetic guidance device 1 that generates a magnetic field for inducing the capsule endoscope.

The magnetic guidance device 1 includes, as its main components, guidance coil groups (X1, X2, Y1, Y2, Z1, Z2, D1, D2, D3, D4, D5, D6, D7, and D8), a guidance coil power source 2, a guidance control unite 3, a controller 4, a sensing coil unit 5 (5a to 5i), a position detector 6, a receiving antenna unit 7 (7a, 7b, and 7c), an antenna selector 8, a receiving unit 9, a display unit 10, a drive coil 11, and a drive-coil operating unit 12.

Each of the fourteen guidance coil groups (X1, X2, Y1, Y2, Z1, Z2, D1 to D8) has an air-core electromagnet and forms an induction magnetic field generation unit. Guidance coils according to the present embodiment are disposed on the sides of a rectangular parallelepiped. As indicated by the arrow in FIG. 1, the direction in which the capsule endoscope 21 is moved forward or backward direction (or the direction to which the human body used as a sample moves) is assumed to correspond to the X-axis direction. The direction horizontally perpendicular to the X-axis is defined as Y-axial direction, and the direction vertically perpendicular to the X-axis (i.e., the direction of gravity), as Z-axial direction.

In these axis directions, the guidance coils X1 and X2 are placed oppositely around the surfaces of front and rear sides, forming magnetic lines of force in the X-axis direction, and becoming vertical to the X-axis direction. In a description below, the guidance coil X1 side is assumed as a forward direction, and the guidance coil X2 side, as a backward direction. In addition, movement from the guidance coil X2 to the guidance coil X1 refers to forward movement, and its reverse, backward movement. The guidance coils Y1 and Y2 are disposed opposite to each other along the perimeters of both side faces perpendicular to the Y-axis, and generate magnetic lines of force along the Y-axis. The guidance coils D3 and D7 are disposed on one of the side faces and inside the guidance coil Y1 so as to divide this face into two. The guidance coils D1 and D5 are disposed on the other (i.e., opposite) of the side faces and inside the guidance coil Y2 so as to divide this face into two.

Similarly, the guidance coils Z1 and Z2 are disposed opposite to each other along the perimeters of both upper and lower faces perpendicular to the Z-axis, and generate magnetic lines of force along the Z-axis. The guidance coils D4 and D8 are disposed on the upper face and inside the guidance coil Z1 so as to divide this face into two. The guidance coils D2 and D6 are disposed on the lower (i.e., opposite) face and inside the guidance coil Z2 so as to divide this face into two. In a description below, the guidance coil Z1 side is assumed as an upward direction and, the guidance coil Z2 side, as a lower direction. In addition, movement from the guidance coil Z2 to the guidance coil Z1 refers to upward movement, and the reverse of it, downward movement.

The guidance coil groups are supplied with, for example, an alternating current, thereby generating an alternating magnetic field. This alternating magnetic field includes one or more components of a frequency near resonance frequency produced by a capacitor 33 and a coil (i.e., magnetic induction coil 31) (described below) disposed in the capsule endoscope 21, an alternating magnetic field generated by the drive coil 11 acts on the magnetic induction coil 31, thereby generating an induction current. Consequently, a magnetic field is generated from the magnetic induction coil. The induction magnetic field thus generated is detected by the plurality of sensing coils 5a to 5i, thereby producing a signal including position information, which will be transmitted to the position detector 6. Based on this signal, the position detecting device calculates the position of the capsule endoscope 21 and information about its position. The position and position information are transmitted to the guidance control unite 3, and used for calculation that determines a magnetic field to be generated by the guidance coil groups.

The group of guidance coils X1, X2, Y1, Y2, 21, Z2 and D1 to D8 constitutes first magnetic gradient generating means, which generates a magnetic gradient (first magnetic gradient) that acts on a magnet (magnetic substance) in the capsule endoscope 21, thereby moving the magnet forward/backward or upward/downward, or left/right, and pulling the magnet in a desired direction.

When the guidance coil groups pull the capsule endoscope 21 in a desired direction by moving the capsule endoscope 21 upward, the guidance coil Z1 generates magnetic gradient (second magnetic gradient) that acts on the magnet in the capsule endoscope 21 so as to cancel force of moving the capsule endoscope 21 downward, exerted on account of the gravity. Thus, the guidance coil eliminates the effect of the gravity. The guidance coils D4 and D8 may be allowed to act in the same manner as the guidance coil Z1. This guidance coil Z1 constitutes second magnetic gradient generating means, which eliminates the effect of gravity acting on the capsule endoscope 21 being moved in a desired direction. On the other hand, when the guidance coil groups pull the capsule endoscope 21 in a desired direction by moving the capsule endoscope 21 downward, the guidance coil Z2 generates magnetic gradient that acts on the magnet in the capsule endoscope 21 so as to cancel buoyancy causing the capsule endoscope 21 to float. Thus, the guidance coil Z2 eliminates the effect of buoyancy. The guidance coils D2 and D6 may be allowed to act in the same manner as the guidance coil Z2.

Specifically, the pair of opposite guidance coils X1 and X2, the pair of Y1 and Y2, and the pair of Z1 and Z2 each generate a magnetic field in the same direction within a space surrounded by the guidance coils, thereby generating a uniform magnetic filed. If the guidance coils of each pair generate magnetic fields in directions opposite to each other, an inclined magnetic field can be generated. Driving, as necessity requires, the guidance coils D1 to D8 in the same manner as described above makes it possible to generate a highly uniform magnetic filed, gradient magnetic field or the like. Accordingly, the independent control of the fourteen guidance coils allows the generation of a magnetic field of a desired magnetic field intensity and of a desired magnetic gradient in a desired space.

Such a configuration of the guidance coil groups enables the capsule endoscope 21 not only to move forward/backward, upward/downward, or leftward/rightward, but also to incline by means of the group of guidance coils X1, X2, Y1, Y2, Z1, Z2, and D1 to D8 in combinations. For example, by generating a magnetic field so that the leading end and trailing end of the capsule endoscope 21 are oriented upward and downward, respectively, the capsule endoscope 21 can be put in an oblique position with its forward end pointing upward.

These guidance coils are connected to the guidance coil power supply 2 that are independently driven. These guidance coil power supplies 2 are controlled by commands given by the guidance control unite 3, and suitably supply power to the corresponding guidance coils used to generate a desired magnetic field in a desired space.

In this embodiment, a position detection system (a position detecting means) for detecting information about a position (spatial position) of the capsule endoscope 21 comprises a drive coil 11 for generating an induction magnetic field in the coil provided in the capsule endoscope 21, a sense coil group 5 for detecting the induction magnetic field generated in the capsule endoscope 21, a position detector 6 for generating the information about a position of the capsule endoscope 21 (the position in a three-dimensional space and the direction of the capsule endoscope) from the signal based on the induction magnetic field received by the sense coil group 5, and a drive coil driver 12 for driving the drive coil 11 according to an instruction from the position detector 6.

The nine sense amplifiers 5a-5i composing the sensing coil group 5 are evenly disposed within a plane parallel to the side face on which the guidance coil Y1 is disposed, so as to ensure the accurate position and position of the capsule endoscope 21. The present embodiment exemplifies the case where a combination of the sensing coil group 5 and the drive coil 11 disposed opposite to each other detects a position along the Z-axis. However, in order to detect a three-dimensional position and position, it is preferable to dispose another combination, for example, on the upper face, and yet another combination, on the side face perpendicular to the upper face. In order to further improve accuracy of detection, it is preferable that the number of sensing coils be somewhat larger.

The position detector 6 receives an instruction to specify a timing of detecting the information about a position from the guidance control unit 3, and drives the drive coil driver 12 based on the instruction.

The drive-coil operating unit 12 supplies an alternating current to the drive coil 11, thereby producing a magnetic field. Thus, an induction magnetic field is generated by the capsule endoscope 21 located in the magnetic field. Each sensing coil of the sensing coil group 5 detects a signal based on the induction magnetic field generated by the capsule endoscope 21, and outputs the corresponding signal to the position detector 6. The position detector 6 creates, from the signal based on the induction magnetic field, information about the position and position of the capsule endoscope 21, and then outputs this information to the guidance control unite 3. Taking account of the information about the position and posture of the capsule endoscope 21, which has been output from the position detector 6, the guidance control unite 3 determines the desired moving direction, and instructs the guidance coil power supply 2 to generate a magnetic field appropriate for such movement. Following the instruction from the guidance control unite 3, the guidance coil power supply 2 cause the corresponding guidance coil groups X1, X2, Y1, Y2, Z1, Z2 and D1 to D8 to produce a current. Consequently, the magnetic field appropriate for the movement is generated by the guidance coil group, thus making it possible to smoothly induce the capsule endoscope 21.

The controller 4 serves as an input device that specifies the moving direction or gradient of the capsule endoscope 21 by inclining an input operation part, such as a joystick, operated in a given direction by an operator. Instead of the joystick, various members, such as a sight line input device, a touch panel, and buttons disposed so as to allow moving in all directions, can also be used as an input operation part for the controller 4.

The guidance control unite 3 receives instruction signals from the controller 4, position and posture information from the position detector 6, and signals relating to the driven state of each guidance coil from the receiving unit 9, and then calculates a magnetic force (magnetic field) for moving the capsule endoscope 21 to a desired position. The guidance control unite 3 also calculates magnetic forces that must be produced by the guidance coil groups X1, X2, Y1, Y2, Z1, Z2 and D1 to D8 in order to generate the magnetic force.

Then the control unite 3 transmits commands to the corresponding guidance coil power sources.

During a communication period, during which image data acquired by the capsule endoscope 21 is transmitted to the receiving unit 9, the guidance control unite 3 stops generation of the magnetic field. Simultaneously with this, during the communication period, the position detector 6 operates the drive coils 11 based on instruction from the guidance control unite, thereby capturing position information from the sensing coil group 5.

Three receiving antennas 7 are connected to the receiving device via the antenna selector 8, which performs a selection operation. These receiving antennas 7 are: a receiving antenna 7a (AX) that receives information about the inside of a body together with image data, from the axial X direction; a receiving antenna 7b (AY) that receives information about the inside of the body from the axial direction Y; and a receiving antenna 7c (AZ) that receives information about the inside of the body from the axial direction Z. Thus, the receiving antennas 7 can detect information about the inside of a body in three axial directions.

The antenna selector 8 selects the antenna 7a, 7b, or 7c to be used for communication. The antenna selector 8 receives the intensity and direction of a magnetic field generated in the place of each receiving antenna by the guidance coil group, and the degree of a magnetic field gradient; distinguishes the receiving antenna that is least affected by the magnetic field from the other antennas; and selects this receiving antenna. Selecting this receiving antenna 7 stabilizes communications between the capsule endoscope 21 and receiving unit 9.

A signal indicating the timing of receiving information about the inside of a body from the capsule endoscope 21 is transmitted to the guidance control unite 3 by the receiving unit 9. As described above, the guidance control unite 3 stops the guidance coil group and drive coil 11 from generating an induction magnetic field during the communication period, which is the period during which information about the inside of the body (image data) is transmitted. This stopping process makes it possible for the receiving device to receive information about the inside of a body from the capsule endoscope 21 without being affected by an induction magnetic field. This stopping process prevents the communication period from coinciding with a moving period and position detecting period. Accordingly, this eliminates the effects of noise upon the information about the inside of a body and of an induction magnetic field upon the receiving antennas.

Accordingly, in the case where the intensity and gradient of a magnetic field generated near the capsule endoscope 21 or receiving antenna 7 are great, this stopping process is effective in preventing noise from affecting image data and also in eliminating the effect of an induction magnetic field on the receiving antennas. Even in the case where the intensity of a magnetic field generated from any of the guidance coils is high, the position detector 6 can be properly operated.

The display unit 10 consists of a liquid crystal display, and displays an image generated by the receiving unit 9 and shot by the capsule endoscope 21. When the image is displayed, the data such as imaging situation related to the displayed image may be displayed on the screen together with the image. There will next be described an example of the configuration of the capsule endoscope 21 according to the embodiment with reference to FIGS. 2 to 5.

FIG. 2 is a sectional view of the configuration of the capsule endoscope according to the present embodiment.

A capsule container 23 of the capsule endoscope 21 includes a transparent semispherical leading-end container 23a on the front end side; and an infrared-transparent trailing-end container 23b with an exactly cylindrical shape becoming semispherical towards the trailing end. The capsule container 23 accommodates a capsule endoscope body (described below) and is closed tightly so as to be impervious to water. The direction in which the capsule container 21 is propelled is, for example, in the axial direction of the cylinder, as indicated by reference letter C in FIG. 2.

The capsule endoscope body will now be described.

The capsule endoscope body is roughly divided into: an imaging unit for imaging the medial wall of an intracavital; a power source unit for driving the imaging unit; an induction magnetic field generation unit for generating an induction magnetic field by means of the drive coil 11 described above; a drive magnet for driving the capsule endoscope 21; and a transmission unit for transmitting information (communication data) about the inside of a body to the receiving antennas 7 together with the data of the image picked up.

The imaging unit includes: imaging optics 26 having a fixed focusing lens; an imaging element 25 composed of a CMOS, a CCD, etc., mounted on an imaging-side substrate 24a; an illuminating unit 39 disposed near the imaging optics 26 and having LEDs the light from which can be modulated; and an image processing circuit 27 disposed on the back of the imaging-side substrate 24a relative to the imaging element 25 and used to subject an image signal from the imaging element 25 to a predetermined imaging process. The imaging-side substrate 24a, a power-source-side substrate 24b, and a front battery-substrate 43a are integrally fixed by being sealed in a bonding unit 29 with an adhesive.

The power source unit includes: a small battery 32 composed of a button battery or the like; a pair of battery-side substrates 43 (43a, 43b) provided with a power source terminal (not shown) that derives power from the small battery 32; a heat-shrinkable tube 34 fixing the small battery 32 between the battery substrates; the power-source-side substrate 24b, the circuit wiring of which is electrically connected to the circuit wiring of the imaging-side substrate 24a by means of a flexible substrate or the like; and a power source circuit 28 disposed on the power-source-side substrate 24b and supplied with the power of the small battery 32.

The magnetic field generation unit includes: a magnet 30 disposed on the perimeter of the bonding unit 29; a magnetic induction coil 31 disposed via the magnet 30; and a capacitor 33 disposed on the battery substrate on the front end side and composing a CL resonance circuit together with the induction coil 31.

This magnetic induction coil 31 is formed in the shape of a ring of the maximum outside shape slightly smaller than the inside diameter of the capsule container 23. The magnet 30 causes external magnetic fields to converge onto the magnetic induction coil 31. Examples of the material of the magnet 30 are an amorphous magnetic body and FINE MED (manufactured by Hitachi Metals, Ltd.), which are high in saturated magnetic flux density and magnetic permeability. Such a material formed in a thin film is effective to reduce the volume of the magnet disposed in the capsule endoscope.

Further, disposed on the rear battery-substrate 43b is a disk-shaped driving magnet 42. A preferred example of the material for the magnet 42 is neodymium cobalt but the material is not limited to this. The upper and lower portions of the magnet 42 are polarized N and S respectively so that lines of magnetic force are generated along the Z-axis. Setting the polarities in this manner makes it possible always to orient the capsule endoscope 21 in a fixed direction in relation to the guidance coil groups of the magnetic guidance device 1. Accordingly, the top and bottom of an image picked up can be absolutely determined.

The transmission unit includes: a transmission circuit 36 mounted on the back (magnet 42 side) of a transmission substrate 40; an antenna 37 disposed on the surface (rear-end container 23b) of the substrate 40; a shield part 35 that covers an exposed transmission circuit 36 and confines the magnetic force of the magnet 42; and an optical switch 38 mounted on the antenna 37 side of the transmission substrate 40 and used to turn the capsule endoscope on or off.

In such a configuration, the direction in which the polarities of the magnet 42 are set and the direction of the antenna 37 connected to the transmission circuit 36 are made different by 90° in order to satisfy conditions for making the entry direction of a magnetic field generated by the magnet 42 different from the direction of the antenna 37 by 90°. Thus, the effect of magnet 42's field on the antenna 37 is minimized.

The shield part 35 is made of a magnetic material and absorbs magnetic fields near the antenna 37. This reduces the intensity of any magnetic field entering the antenna 37, and minimizes the effect of a magnetic field on radio communication between the transmission circuit 36 and antenna 37, and thus ensuring stable radio communication.

The optical switch 38 senses infrared rays and the like. At least part of the trailing-end container 23b of the capsule container 23, which part is near the optical switch, is made of a material that transmits infrared rays (of a wavelength sensitive to the optical switch). By emitting infrared rays onto the optical switch 38 from an infrared ray emitting device (not shown), the optical switch 38 should be turned on, power is then supplied to the capsule endoscope from the small battery 32 via the power source circuit, and the capsule endoscope is consequently activated to initiate an imaging process and a transmission process. This circuit of the optical switch 38 is configured to allow a toggle operation. Accordingly, after infrared rays are once emitted to the optical switch, the capsule endoscope maintains an on-state. The circuit of the optical switch 38 may be configured such that the capsule endoscope is turned off by re-emitting infrared rays onto the optical switch when the switch is in the on-state.

The shield part 35 covering the transmission circuit 36 minimizes the effect of the intensity of magnet 42's magnetic field on the transmission circuit and radio circuit (e.g., superposed noises or a shorter communicative distance). Thus, sharper image data with less noise can be transmitted to the receiving unit 9.

Next, there will be described operation of the capsule endoscope 21 and magnetic guidance device 1 of the encapsulated medical device guidance system according to the present embodiment.

As described above, magnetic fields with magnetic gradients, simultaneously generated by the plural guidance coils, are superposed, thereby generating one magnetic field, which moves the capsule endoscope 21. The magnetic field intensity or magnetic gradient for inducing the capsule endoscope 21 are very large, compared to an electric wave (electromagnetic wave) corresponding to information about the inside of the body transmitted by the capsule endoscope 21. If a signal exceeding the input allowable range of the receiving elements (e.g., preamplifier) of the receiving unit 9 is transmitted and an induction current is applied, the receiving elements can be damaged. If a magnetic field (group of lines of magnetic force) changes very suddenly on account of the superposed state of the magnetic gradients of the lines of magnetic force produced by the plurality of guidance coils, the capsule endoscope 21 may suddenly move. Consequently, considerable induced voltage may be produced in the coil forming the transmission antenna 37 of the capsule endoscope 21, resulting in a severe overload being applied to the transmission circuit. Even if the overload does not go beyond the electrical resistance of the components, radio communication may fail.

In order to prevent induced voltage from applying overload current to the receiving device, the present embodiment selectively disconnects any receiving antenna of the magnetic guidance device 1, which has been affected by a magnetic field inducing the capsule endoscope 21, or in which an overload current caused by induced voltage is flowing. Next, a description will be given of the configuration of a circuit that includes the function of preventing overload current, caused by induced voltage arising from a sudden movement of the capsule endoscope 21 or sudden change in magnetic field gradient, from being applied to the transmission circuit 36 of the capsule endoscope 21 and the receiving unit 9 of the magnetic field generation device 1.

The magnetic guidance device 1 according to the present embodiment includes three receiving antennas 7 (AX, AY, and AZ) that have directionalities along the axes X, Y, and Z respectively, as shown in FIG. 1. The description below exemplifies the relation between the guidance coil Y2 and the receiving antennas 7 (AX, AY, and AZ).

First, there will be described a first control method for preventing receiving of overload current caused by induced voltage, by selecting an appropriate one among the plural receiving antennas.

Lines of magnetic force generated by the guidance coil Y2 supplied with power pass the receiving antennas AX, AY, and AZ, as shown in FIG. 3. In one of these receiving antennas, AY, lines of magnetic force are parallel to the directionality of this antenna. In this receiving state, an overload current may flow in the receiving antenna AY on account of induced voltage caused by a magnetic field generated by the guidance coil Y2. Lines of magnetic force enter the other receiving antennas AX and AZ at approximately 90° relative to their respective directionalities, as shown in FIG. 3. Accordingly, almost no overload current caused by induced voltage due to a magnetic field generated by the guidance coil Y2 flows in the receiving antennas AX and AZ, thus making it possible to accurately capture information about the inside of a body from the capsule endoscope 21. If an overload current caused by the most intense induced voltage flows in the receiving antenna AY, information about the inside of the body, which is actually necessary, may not be captured from the capsule endoscope 21.

Thus, the receiving antenna subjected to the most intense induced voltage by a magnetic field on account of the directionality of the receiving antenna is distinguished from the others, and the one ensuring accurate receiving can be selected. In this embodiment, the antenna selector 8 is provided for antenna selection. As long as the receiving antennas AX and AX allow accurate receiving, either one of them is selected, thus making it possible to receive information about the inside of a body together with accurate image data from the capsule endoscope 21. This embodiment exemplifies the case where three receiving antennas are disposed so as to have directionalities along the three axes perpendicular to one another. However, the invention is not limited to this and, even if the receiving antennas are oriented in the same direction, similar control can be achieved by taking the directions of lines of magnetic force into consideration.

Figure 4:
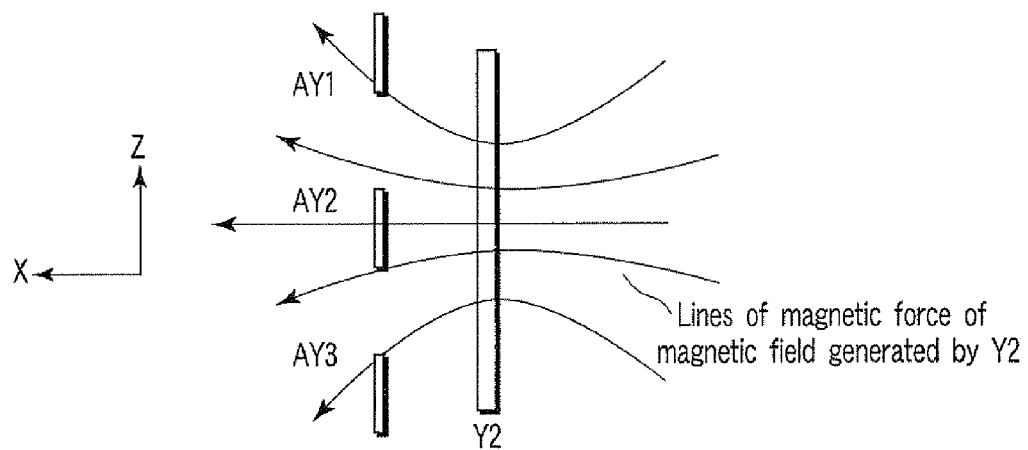
FIG. 4 shows an interrelation between a modified receiving antenna according to the embodiment and lines of magnetic force generated by a guidance coil.

FIG. 4 shows a modified example in which three receiving antennas 7 (AY1, AY2 and AY3) are disposed in the same direction.

Of these, the receiving antenna AY2 is disposed in the middle of the three and right opposite to the middle of the guidance coil Y2. On account of this positional relation, the directionality of the receiving antenna AY2, in which receiver sensitivity is highest, coincides with the direction of lines of magnetic force of a magnetic field generated by the guidance coil Y2.

As a result, an overload current caused by the induced voltage of the guidance coil Y2 may flow to excess in the receiving antenna AY2, leading to failure in communication with the capsule endoscope 21. Compared to AY2, the receiving antennas AY1 and AY3 receive lines of magnetic force from oblique directions, thus restraining overload currents caused by induced voltage, and hence ensuring accurate receiving of information about the inside of a body from the capsule endoscope 21.

Arranging the plural receiving antennas 7 along the same axis at arbitrary intervals and selecting a suitable one from them makes it possible constantly to receive accurate information about the inside of a body transmitted from the capsule endoscope 21.

Also, in a magnetic field generated by superposing lines of magnetic force simultaneously generated by a plurality of guidance coils, as described above, the receiving antennas are evaluated based on the direction and intensity of the magnetic field. Normal communication can be maintained by selecting the receiving antenna into which a line of magnetic force enters at an angle closest to 90° relative to the directionality of the receiving antenna. In order to select a preferred receiving antenna, it is preferable that the intensity of and rate of change in a magnetic field generated in proximity to each receiving antenna be evaluated taking the entry direction of the magnetic field into consideration.

An overload current I caused by induced voltage is defined by a relation expressed by the following formula, $I \propto (dH/dt) \cdot \cos(\theta)$, wherein H represents the intensity of a magnetic field generated by a plurality of magnetic field generating devices in proximity to a receiving antenna, and $\theta$ represents an angle between the magnetic field and the directionality of the receiving antenna. The $dH/dt$ represents the rate of change in the magnetic field. However, since the magnetic field is generated by a device that generates a magnetic field in a limited space, dH/dt increases with an increase in H. Accordingly, H can be used as substantially equivalent to dH/dt.

A specific method for selecting a receiving antenna 7 will now be described.

1) After the guidance control unite 3 obtains a magnetic field through calculation or the like, the intensity of the magnetic field to be generated by each guidance coil power source 2 (or guidance coil) is determined. 2) The intensity of the magnetic field (the rate of change in the magnetic field) generated in proximity to each receiving antenna 7 and the direction of the magnetic field are obtained. 3) A coefficient proportional to an induction current flowing in each receiving antenna 7 is obtained. Alternatively, the angle between the directionality of each receiving antenna and the magnetic field is obtained. 4) The antenna selector 8 selects the receiving antenna with the smallest coefficient proportional to an induction current (an overload current caused by induced voltage). Alternatively, the antenna selector 8 selects the receiving antenna in which the angle between the directionality and the magnetic field is closest to 90°.

Thus, the antenna selector 8 selects the receiving antenna least subjected to the application of overload current caused by induced voltage generated by an guidance coil in order to perform position guidance or position control for the capsule endoscope, as described above.

Next, there will be described the configuration of a circuit that has the function of preventing an overload current caused by induced voltage from being applied to the transmission circuit 36 of the capsule endoscope 21 and to the receiving unit 9 of the magnetic field generating device 1. First, the transmission circuit 36 of the capsule endoscope 21 will be described below.

Figure 5:
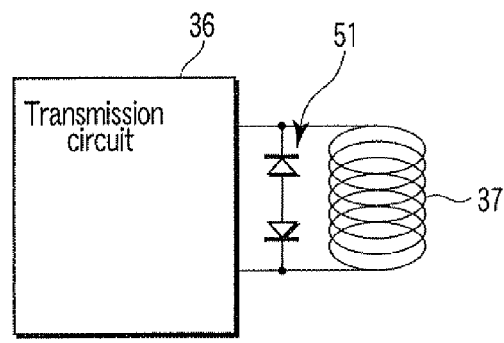
FIG. 5 shows the circuit structure of a first example in which a function according to the embodiment is provided in order to prevent the application of overload current caused by induced voltage.

FIG. 5 shows a first example in which a Zener diode array (a series of Zener diodes) 51 is inserted between both ends of a coil forming the transmission antenna 37 of the capsule endoscope 21. In this Zener diode array 51, the anodes of the two Zener diodes are connected so as to cope with an alternating current signal, and their cathodes are connected to the corresponding ends of the coil 37.

In this configuration, if overload current caused by induced voltage reaches or exceeds a prescribed threshold, this current flows through the Zener diodes. Accordingly, the current flowing into the transmission circuit 36 can be limited and hence damage to the circuit can be prevented.

Figure 6:
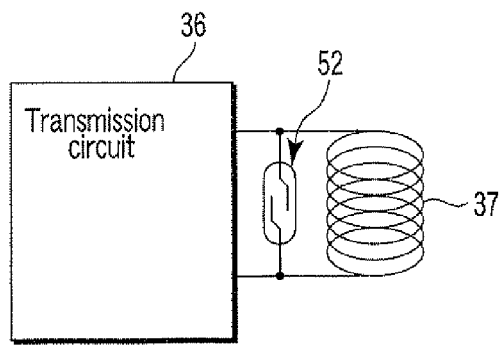
FIG. 6 shows the circuit structure of a second example in which a function according to the embodiment is provided in order to prevent the application of overload current caused by induced voltage.

FIG. 6 shows a second example in which a lead switch 52 is inserted between both ends of the coil forming the transmission antenna 37 of the capsule endoscope 21. In this configuration, if a magnetic field reaches or exceeds a prescribed threshold, the lead switch 52 is turned on and consequently a current flows into it. This makes it possible to limit the flow of current into the transmission circuit 36 and hence prevent damage to the circuit. In this second example, the induced voltage is not directly monitored. However, when a greater induced voltage is caused, a greater magnetic field is usually generated and accordingly, effects may occur similar to those in the first example.

Next, there will be described the receiving unit 9 of the magnetic field generation device 1.

Figure 7:
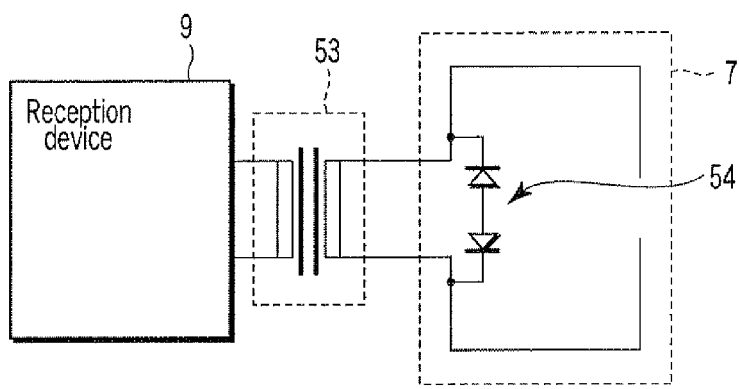
FIG. 7 shows the circuit structure of a third example in which a function according to the embodiment is provided in order to prevent the application of overload current caused by induced voltage.

FIG. 7 shows a third example in which a Zener diode array (a series of Zener diodes) 54 is inserted between both ends of each receiving antenna 7 (AY1, AY2, AY3) of the receiving unit 9. The receiving antennas 7 are connected to the input terminal of the receiving unit 9 via a transformer 53. In the Zener diode array 54, the two anodes of the Zener diodes are connected, and their cathodes are connected to the corresponding ends of the receiving antennas 7. The input and output of the transformer 53 are electrically equivalent.

In such a configuration, if induced voltage reaches or exceeds a prescribed threshold, a current flows through the Zener diodes. This limits the current flowing into the receiving unit 9 and prevents damage thereto.

Figure 8:
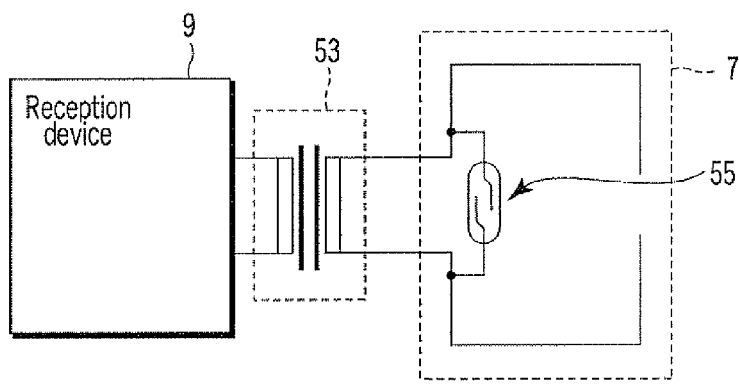
FIG. 8 shows the circuit structure of a fourth example in which a function according to the embodiment is provided in order to prevent the application of overload current caused by induced voltage.

FIG. 8 shows a fourth example in which a lead switch 55 is inserted between both ends of each receiving antenna 7 (AY1, AY2, AY3) of the receiving unit 9. If a magnetic field reaches or exceeds a prescribed threshold, a lead switch is turned on and, consequently, an overload current caused by induced voltage flows through the lead switch 55. This limits the current flowing into the receiving unit 9 and prevents damage thereto. In the fourth example, the induced voltage is not directly monitored. However, when a greater induced voltage is caused, a greater magnetic field is usually generated and accordingly, effects may occur similar to those in the third example.

Figure 9:
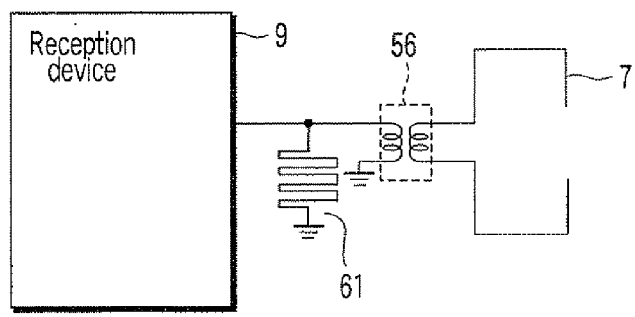
FIG. 9 shows the circuit structure of a fifth example in which a function according to the embodiment is provided in order to prevent the application of overload current caused by induced voltage.

FIG. 9 shows a fifth example in which a $\lambda/4$ stub line 61 is inserted into the input line of the receiving unit 9 connected to each receiving antenna 7 (AY1, AY2, AY3) via a transformer 56. The input and output of the transformer 56 are electrically equivalent.

In the $\lambda/4$ stub line 61, if a short circuit (potential grounding) is formed at one end of it with a $\lambda/4$ stub of a transmission line in relation to a wavelength $\lambda$ used in a radio circuit, the other end is open. The impedance of such a short stub is $Z=j*Z0*\tan(\beta l)$, wherein Z0 is the characteristic impedance of the stub line 61, $\beta$ is a phase constant of $2\pi/\lambda$, and l is the length of the stub line 61. If $l=\lambda/4$, the impedance Z is $Z=j*Z0*\tan(\pi/2)=\infty$ (infinite).

Accordingly, the radio circuit operated at % is not affected at all, and the other frequencies are short-circuited. If the component of the frequency corresponding to a sudden change in a magnetic field does not reach the frequency of radio communication, a voltage surge can be avoided by this $\lambda/4$ stub line 61. Therefore, if induced electromagnetic force arises, overload current flowing in the input line is caused to flow into an installation and, thus, damage to the receiving unit 9 is prevented.

Figure 10:
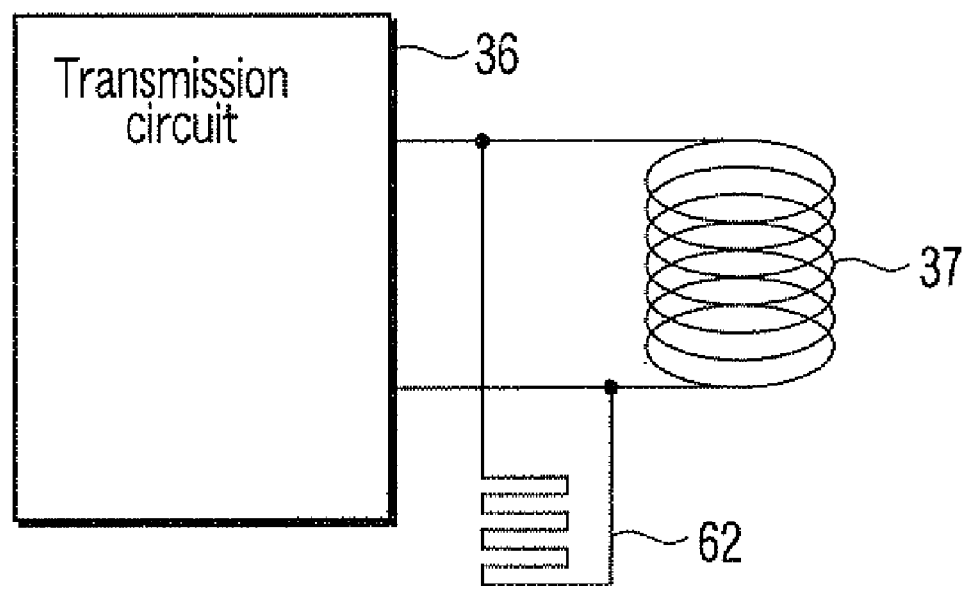
FIG. 10 shows the circuit structure of a sixth example in which a function according to the embodiment is provided in order to prevent the application of overload current caused by induced voltage.

FIG. 10 is a sixth example in which a $\lambda/4$ stub line 62 is inserted between both ends of the transmission antenna 37 of the transmission circuit 36. Since the $\lambda/4$ stub line 62 identical to that in the fifth example is provided, overload current caused by induced voltage is short-circuited. This limits the current flowing into the transmission circuit 36 and prevents damage to the transmission circuit 36.

The present invention can, therefore, provide an encapsulated medical device guidance system which includes a plurality of receiving antennas of different directionalities and selects a receiving antenna appropriate to receive information about the inside of a body transmitted from an encapsulated medical device.

What is claimed is:

1. An encapsulated medical device guidance system comprising:
   an encapsulated medical device having an internal biological information acquisition unit to acquire internal biological information, a communication unit to output the acquired internal biological information to the outside as an output signal, and a magnet;
   a plurality of receiving antennas which are different from one another in a direction in which receiver sensitivity in a directionality thereof is highest and receive the output signal;
   a selector which is connected to the plurality of antennas and selects a selected receiving antenna as a path for the output signal;

a receiving device which is connected to the selector and receives the output signal from the selected receiving antenna;

a magnetic field generating unit which generates an induction magnetic field for acting upon the magnet and moving the encapsulated medical device in a target direction; and a control unit which controls the magnetic field generating unit, wherein the control unit controls the selector to selectively disconnect from the receiving device an affected receiving antenna of the plurality of receiving antennas in which the induction magnetic field generated by the magnetic field generating unit has caused an overload current to flow.

2. The system according to claim 1, wherein the control unit calculates an angle between the direction of the induction magnetic field generated by the magnetic field generation unit and the directionality of each of the plurality of receiving antennas and controls the selector to select as the selected receiving antenna the most nonparallel of the plurality of receiving antennas based on the result of the calculation.

3. The system according to claim 1, wherein a magnetic lead switch is connected to both terminals or electrically equivalent terminals of at least one of the plurality of receiving antennas.

4. The system according to claim 1, wherein a Zener diode array is connected to both terminals or electrically equivalent terminals of at least one of the plurality of receiving antennas.

5. The system according to claim 1, wherein a short stub composed of a transmission line is connected to both terminals or electrically equivalent terminals of at least one of the plurality of receiving antennas.

6. The system according to claim 1, wherein the communication unit includes a transmission antenna, and a magnetic lead switch is connected to both terminals or electrically equivalent terminals of the transmission antenna.

7. The system according to claim 1, wherein the communication unit includes a transmission antenna, and a Zener diode array is connected to both terminals or electrically equivalent terminals of the transmission antenna.

8. The system according to claim 1, wherein the communication unit includes a transmission antenna, and a short stub composed of a transmission line is connected to both terminals or electrically equivalent terminals of the transmission antenna.

9. The system according to claim 1, wherein the communication unit has a shield part made of a magnetic material.

10. A method for controlling a system for guidance of an encapsulated medical device which transmits acquired internal biological information while moved in a target direction within the body cavity by movement of a magnet disposed in the encapsulated medical device by a magnetic field, wherein one of a plurality of receiving antennas oriented in different directions is selected according to receiver sensitivity to the transmitted information about the inside of the body, thereby receiving the acquired internal biological information, and any selected receiving antenna of the plurality of receiving antennas is disconnected from a receiving path if the magnetic field has caused an overload current to flow in the selected receiving antenna.

11. The method according to claim 10, wherein an angle between a direction in which the receiver sensitivity to the generated induction magnetic field is the highest and a direction of a directionality of each of the plurality of receiving antennas is calculated, and a selected receiving antenna determined to be the most nonparallel is selected to receive a signal.

* * * * *